United States Patent [19]
Aung et al.

[11] Patent Number: 5,791,348
[45] Date of Patent: Aug. 11, 1998

[54] AUTOMATIC BLOOD PRESSURE MEASURING SYSTEM

[75] Inventors: Ye Aung. Komaki; Hideo Nishibayashi. Inuyama. both of Japan

[73] Assignee: Colin Electronics Co., Ltd.. Aichi-ken, Japan

[21] Appl. No.: 592,611

[22] Filed: Jan. 26, 1996

Related U.S. Application Data

[63] Continuation of Ser. No. 829,325, Feb. 3, 1992, abandoned.

[30] Foreign Application Priority Data

Mar. 1, 1991 [JP] Japan .................................. 3-061205

[51] Int. Cl.⁶ ...................................................... A61B 5/00
[52] U.S. Cl. ........................ 128/680; 128/681; 128/682
[58] Field of Search ................................. 128/668, 677, 128/680-3, 687, 672

[56] References Cited

U.S. PATENT DOCUMENTS

| | | | |
|---|---|---|---|
| 4,696,151 | 9/1987 | Utsunomiya et al. | 128/682 |
| 4,870,973 | 10/1989 | Ueno . | |
| 4,872,461 | 10/1989 | Miyawaki | 128/682 |
| 4,905,704 | 3/1990 | Walloch | 128/681 |
| 4,924,874 | 5/1990 | Murase . | |
| 4,928,701 | 5/1990 | Harada et al. | 128/681 |
| 5,099,853 | 3/1992 | Uemura et al. | 128/681 |

FOREIGN PATENT DOCUMENTS

| | | |
|---|---|---|
| 0 298 620 | 1/1989 | European Pat. Off. . |
| 0 333 332 | 9/1989 | European Pat. Off. . |
| 0 401 382 | 12/1990 | European Pat. Off. . |

*Primary Examiner*—Robert L. Nasser
*Attorney, Agent, or Firm*—Oliff & Berridge

[57] ABSTRACT

An automatic blood pressure measuring system employs an oscillometric method. a cuff applying pressure to an arterial vessel and then gradually reducing the pressure. On a distal side of the cuff. as seen from the heart of the subject. a pulse wave sensor presses against a distal section of the vessel. If the pulse wave sensor detects a pulse wave from the distal section of the vessel after the force applied by the cuff reaches a first target value. indicating that the initial pressure was insufficiently low. the force is increased to a second target value. After determining a relationship between the blood pressure and the magnitude of the pulse wave detected by the pulse wave sensor, blood pressure can be monitored by the pulse wave sensor.

14 Claims, 3 Drawing Sheets

AUTOMATIC BLOOD PRESSURE MEASURING SYSTEM

This is a Continuation of application Ser. No. 07/829,325 filed Feb. 3, 1992, now abandoned.

BACKGROUND OF THE INVENTION

1. Field of the Invention

The present invention relates to an automatic blood pressure measuring system of the oscillometric type and more particularly to such an apparatus which is adapted to measure a blood pressure of a living subject when the pressing force applied to an artery of the subject is decreased.

2. Related Art Statement

There is known an automatic blood pressure measuring system for measuring a blood pressure of a living subject by the oscillometric method in which a blood pressure of the subject is determined by utilizing a pulse wave consisting of pulses produced from an artery of the subject in synchronism with heartbeat of the subject. The known apparatus includes (a) a pressing device pressing a body portion of a subject and thereby pressing an artery extending in the body portion of the subject, (b) pressure regulating means regulating the pressing force or pressure produced by the pressing device, and (c) determining means controlling the regulating means to increase the pressure of the pressing device to a target pressure (for example, 180 mmHg, or a pressure higher by a suitable amount than a systolic blood pressure of the subject measured in a preceding cycle), collecting pulses of a pulse wave which are produced from the artery and transmitted to the pressing device when the pressure applied to the artery is decreased from the target pressure, and determining a blood pressure of the subject by using the collected pulses. This apparatus is adapted to determine, as a mean blood pressure of the subject, a pressure applied to the artery at the time of detection of a pulse having the greatest amplitude of the amplitudes of the pulses collected during the pressure decreasing operation. In addition, the apparatus determines, as a systolic blood pressure of the subject, a pressure applied to the artery at the time of an inflection point of a curve representing variation of the pulse amplitudes with respect to the pressure applied to the artery which point is located on a higher-pressure side of the mean blood pressure, and as a diastolic blood pressure a pressure at the time of an inflection point of the curve which point is located on a lower-pressure side of the mean blood pressure.

However, the known oscillometric blood pressure measuring apparatus suffers from the problem that, if an actual systolic blood pressure of the subject is higher than the target pressure, or if the actual systolic blood pressure is lower than the target pressure but higher than a pressure at the time when the determining means starts collecting the pulses of the pulse wave transmitted to the pressing device during the pressure decreasing operation, the apparatus cannot measure the systolic blood pressure of the subject because the target pressure is insufficiently low. In the case where the apparatus is of a type which determines a systolic blood pressure immediately after determining a mean blood pressure during the pressure decreasing operation, the apparatus cannot identify that the target pressure is insufficiently low until the pressure applied to the artery is decreased to a level equal to the mean blood pressure. Meanwhile, in the case where the apparatus is of a type which determines a blood pressure by using the pulse wave data obtained during the pressure decreasing operation after the pressure decreasing operation has been completed, the apparatus cannot identify that the target pressure is insufficient until the pressure decreasing operation is completed. Therefore, if the target pressure is insufficient, both of these apparatus are required to effect the blood pressure measuring operation again. This leads to increasing the time necessary for completing the blood pressure measuring operation.

SUMMARY OF THE INVENTION

It is therefore an object of the present invention to provide an automatic blood pressure measuring system for, by using the oscillometric method, measuring a blood pressure of a subject when the pressing force applied to an artery of the subject is decreased from a target force, which system finds insufficiency of the target force and eliminates the insufficiency before the blood pressure measurement and thereby effects the blood pressure measurement in a reduced time.

The above object has been achieved by the present invention, which provides an automatic blood pressure measuring system for measuring a blood pressure of a living subject by the oscillometric method in which a blood pressure is determined by utilizing a pulse wave consisting of pulses produced from an arterial vessel of the subject in synchronism with heartbeat of the subject, the apparatus comprising (1) pressing means for pressing a body portion of a subject and thereby pressing an arterial vessel extending in the body portion of the subject, (2) regulating means for regulating the pressing force of the pressing means, (3) determining means for controlling the regulating means to increase the pressing force of the pressing means to a first target force, collecting pulses of a pulse wave which are produced from the arterial vessel and transmitted to the pressing means when the pressing force is decreased from the first target force, and determining a blood pressure of the subject by using the collected pulses, (4) detecting means for detecting a pulse wave from a section of the arterial vessel located on a distal side of the pressing means as seen from the heart of the subject, and (5) increasing means for, if the detecting means detects the pulse wave from the distal arterial vessel after the regulating means has increased the pressing force of the pressing means to the first target force and before the determining means determines the blood pressure of the subject, increasing the pressing force to a second target force greater by a predetermined amount than the first target force.

In the automatic blood pressure measuring system of the oscillometric type constructed as described above, the detecting means detects a pulse wave from a section of the arterial vessel pressed by the pressing means which section is located on a distal side of the pressing means as seen from the heart of the subject, and the increasing means increases, if the detecting means detects the pulse wave from the distal arterial vessel after the regulating means has increased the pressing force of the pressing means to the first target force and before the determining means determines the blood pressure of the subject, the pressing force to a second target force greater by a predetermined amount than the first target force. That the detecting means has detected the pulse wave from the distal arterial vessel after the pressing force has been increased to the first target force and before the blood pressure is determined, means that the first target force is insufficiently low. Thus, the present system identifies whether or not the first target force is insufficiently low, before the blood pressure of the subject is determined. If the first target force is found to be insufficient, the system or increasing means thereof increases the pressing force of the pressing means to the second target force greater by a predetermined additional pressing force than the first target force, thereby eliminating the insufficiency of the pressing force (i.e., first target force) applied to the artery before the blood pressure determination. Thus, the present system completes the blood pressure measuring operation in a reduced time even as compared with a conventional apparatus of the type which identifies whether or not a target pressing force is insufficient after the pressing force applied to an artery of a subject is decreased from the target force to a pressing force corresponding to a mean blood pressure of the subject and, if the target force is found to be insufficient, effects the blood pressure measuring operation all over again.

According to a preferred feature of the present invention, the increasing means continues to increase the pressing force by increments of the predetermined amount until the detecting means does not detect a pulse wave from the distal arterial vessel.

According to another feature of the present invention, the determining means starts collecting the pulses transmitted to the pressing means, at a time when a predetermined time has passed after the decreasing of the pressing force from the first target force is started.

According to yet another feature of the present invention, the pressing means comprises an inflatable cuff which is adapted to be wound around the body portion of the subject, and means for supplying the cuff with pressurized fluid for inflating the cuff an thereby pressing the body portion and the arterial vessel.

In a preferred embodiment of the present invention, the detecting means comprises a pulse wave sensor which is adapted to be pressed against the distal arterial for detecting a pressure pulse wave therefrom.

According to a feature of the above embodiment of the invention, the system further comprising first means for determining a magnitude of the pressure pulse wave which is detected by the pulse wave sensor when the arterial vessel is not pressed by the pressing means, second means for determining a relationship between blood pressure and pulse magnitude by using the blood pressure determined by the determining means and the determined magnitude of the pressure pulse wave, third means for determining a magnitude of each of pulses of the pressure pulse wave which are detected by the pulse wave sensor after the determination of the relationship, and fourth means for determining a blood pressure of the subject by using the determined relationship and the determined magnitude of the each pulse.

According to another feature of the above embodiment of the invention, the determining means determines a systolic and a diastolic blood pressure of the subject, the first means determines a maximum and a minimum magnitude of a pulse of the pressure pulse wave detected by the pulse wave sensor, the second means determines the blood pressure-pulse magnitude relationship by using the systolic and diastolic blood pressures determined by the determining means and the determined maximum and minimum pulse magnitudes, the third means determines a maximum and a minimum magnitude of the each pulse of the pressure pulse wave detected by the pulse wave sensor after the determination of the blood pressure-pulse magnitude relationship, and the fourth means determines a systolic and a diastolic blood pressure of the subject by using the blood pressure-pulse magnitude relationship and the maximum and minimum magnitude of the each pulse of the pressure pulse wave.

According to yet another feature of the above embodiment of the invention, the determining means determines the blood pressure of the subject at predetermined regular intervals of time, the second means updates the blood pressure-pulse magnitude relationship by using each of the blood pressures determined at the regular intervals and a determined magnitude of the pressure pulse wave, the third means determines a magnitude of each of pulses of the pressure pulse wave detected after each updating of the relationship, and the fourth means determines a blood pressure of the subject by using the each updated relationship and the determined magnitude of the each pulse.

According to a further feature of the above embodiment of the invention, the second means determines the blood pressure-pulse magnitude relationship such that blood pressure is a linear function of pulse magnitude.

According to a preferred feature of the above embodiment of the invention, the system further comprises display means for displaying the blood pressure determined by the determining means and the blood pressure determined by the fourth means.

BRIEF DESCRIPTION OF THE DRAWINGS

The above and optional objects, features and advantages of the present invention will be better understood by reading the following detailed description of the presently preferred embodiment of the invention when considered in conjunction with the accompanying drawings, in which.

DETAILED DESCRIPTION OF THE PREFERRED EMBODIMENT

Figure 1:
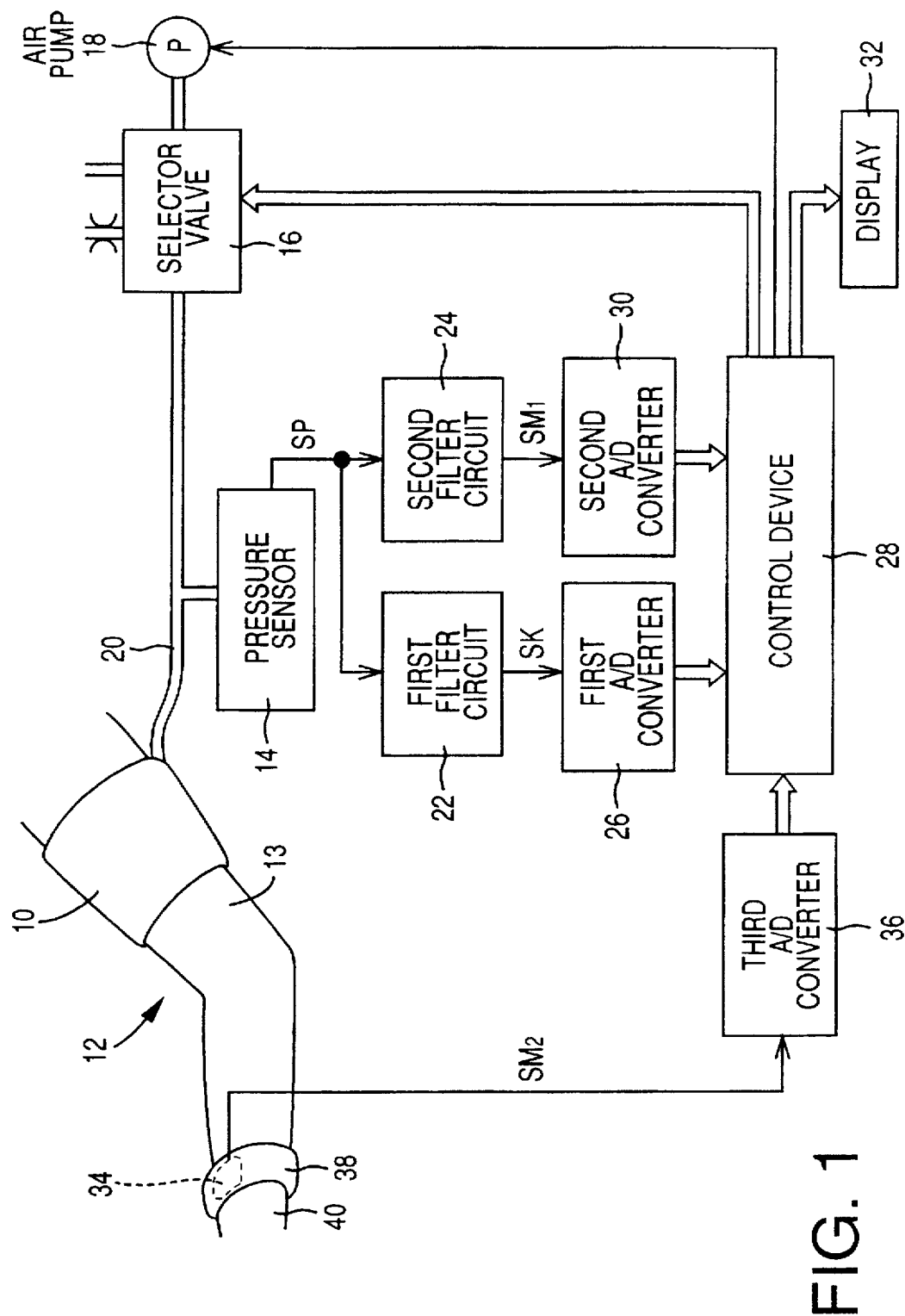
FIG. 1 a diagrammatic view of an automatic blood pressure measuring system of the oscillometric type to which the present invention is applied.

Referring first to FIG. 1, there is shown an automatic blood pressure monitor system of the oscillometric type embodying the present invention. In the figure, reference numeral 10 designates an inflatable cuff formed of rubber. The cuff 10 has a tube-like configuration. The cuff 10 is wound around, for example, an upper portion 13 of an arm 12 of a living subject. The cuff 10 serves as pressing means for pressing the upper arm 13. A pressure sensor 14, a selector valve 16, and an air pump 18 are connected via piping 20 to the cuff 10. The air pump 18 supplies the cuff 10 with pressurized air, thereby increasing an air pressure in the cuff 10. The pressure sensor 14 detects the air pressure in the cuff 10 (hereinafter, referred to as the "cuff pressure P"), and generates a pressure signal SP representing the detected cuff pressure P, to a first and a second filter circuit 22, 24. The first filter circuit 22 includes a low-pass filter which, upon reception of the pressure signal SP, transmits only a cuff pressure signal SK representing a static pressure in the cuff 10. The cuff pressure signal SK is supplied to a control device 28 via a first analog to digital (A/D) converter 26. The second filter circuit 24 includes a band-pass filter which, upon supply of the pressure signal SP, transmits only a pulse wave signal $SM_1$ representing a pressure pulse wave consisting of pulses produced from a brachial artery in synchronism with heartbeat of the subject and transmitted to the cuff 10. The pulse wave signal $SM_1$ is supplied to the control device 28 via a second A/D converter 30. The selector valve 16 is adapted to selectively be placed in a first position thereof (the INFLATION position) in which the valve 16 allows the cuff pressure P to be increased, in a second position thereof (the SLOW-DEFLATION position) in which the valve 16 allows the pressure P to be decreased at a low rate, or a third position thereof (the RAPID-DEFLATION position) in which the valve 16 allows the pressure P to be decreased at a high rate. In the present embodiment, the selector valve 16, air pump 18, and other elements cooperate with each other to serve as regulating means for regulating the pressing force (cuff pressure P) of the pressing means (cuff 10).

The control device 28 includes a so-called microcomputer consisting essentially of a central processing unit (CPU), a read only memory (ROM), a random access memory (RAM), and an input and output port (I/O port). The CPU processes input signals according to control programs pre-stored in the ROM by utilizing the temporary-storage function of the RAM and produces, via the I/O port, drive signals to respective drive circuits (not shown) provided for the selector valve 16 and the air pump 18. In this way, the control device 28 controls the selector valve 16 and air pump 18 for regulating the cuff pressure P. The control device 28 controls the regulating means 16 and 18 for increasing the cuff pressure P to a target pressure, $Pm_a$, and, if a pulse wave sensor 34 (described later) detects a pulse wave after the cuff pressure P has been increased to the target pressure $Pm_a$ and before blood pressure determination is effected, the control device 28 controls the regulating means to increase the cuff pressure P to a second target pressure, $Pm_b$, higher by a predetermined amount than the first target pressure $Pm_a$. In addition, the control device 28 collects pulse wave, or pulses thereof, produced from the brachial artery and transmitted to the cuff 10 when the cuff pressure P is decreased from the first or second target pressure $Pm_a$ or $Pm_b$, and determines a mean, a systolic and a diastolic blood pressure of the subject by using the collected pulses. The control device 28 commands a display 32 such as a cathode ray tube (CRT) to indicate the determined pressure values. The control device 28 iteratively effects this blood pressure determination at predetermined regular intervals of time. In the present embodiment, the control device 28 serves as increasing means for increasing the cuff pressure P to the second target pressure $Pm_b$ higher by the predetermined amount than the first target pressure $Pm_a$.

The pulse wave sensor 34 is connected to the control device 28 via a third A/D converter 36. The pulse wave sensor 34 is secured to the inside surface of an elongate wrist band 38 having a pair of fasteners (not shown) at opposite ends thereof. The wrist band 38 is wound around a wrist 40 of the same arm 12 as the arm pressed by the cuff 10, such that the pulse wave sensor 34 is positioned over the radial artery that is continuous with the brachial artery pressed by the cuff 10 and is located on the distal side of the cuff 10 as seen from the heart of the subject. With the fasteners of the wrist band 38 being fastened with each other around the wrist 40, the pulse wave sensor 34 is pressed with a suitable pressure against the radial artery via skin tissue. The pulse wave sensor 34 is constituted by, for example, a semiconductor strain gauge or a piezoelectric element. The pulse wave sensor 34 detects a pressure pulse wave (hereinafter, referred to as the "distal pulse wave") produced from the radial artery located on the distal side of the brachial artery pressed by the cuff 10. Like the pulse wave transmitted to the cuff 10, the distal pulse wave consists of pulses produced in synchronism with heartbeat of the subject. The pulse wave sensor 34 generates a pulse wave signal $SM_2$ representing the detected distal pulse wave, to the control device 28 via the third A/D converter 36. In the present embodiment, the pulse wave sensor 34 and the wrist band 38 cooperate with each other to serve as detecting means for detecting the distal pulse wave.

The control device 28 determines a maximum and a minimum magnitude of a pulse of the distal pulse wave detected by the pulse wave sensor 34, according to control programs pre-stored in the ROM, and determines a relationship (e.g., a linear function) between blood pressure and pulse magnitude by using the determined maximum and minimum pulse magnitudes and the systolic and diastolic blood pressures actually measured using the cuff 10. According to the blood pressure-pulse magnitude relationship, the control device 28 continuously determines a systolic and a diastolic blood pressure of the subject by using a maximum and a minimum magnitude of each of pulses of the distal pulse wave detected by the pulse wave sensor 34 after determination of the relationship, and commands the display 32 to indicate the blood pressure values determined with respect to the each pulse.

Figure 2:
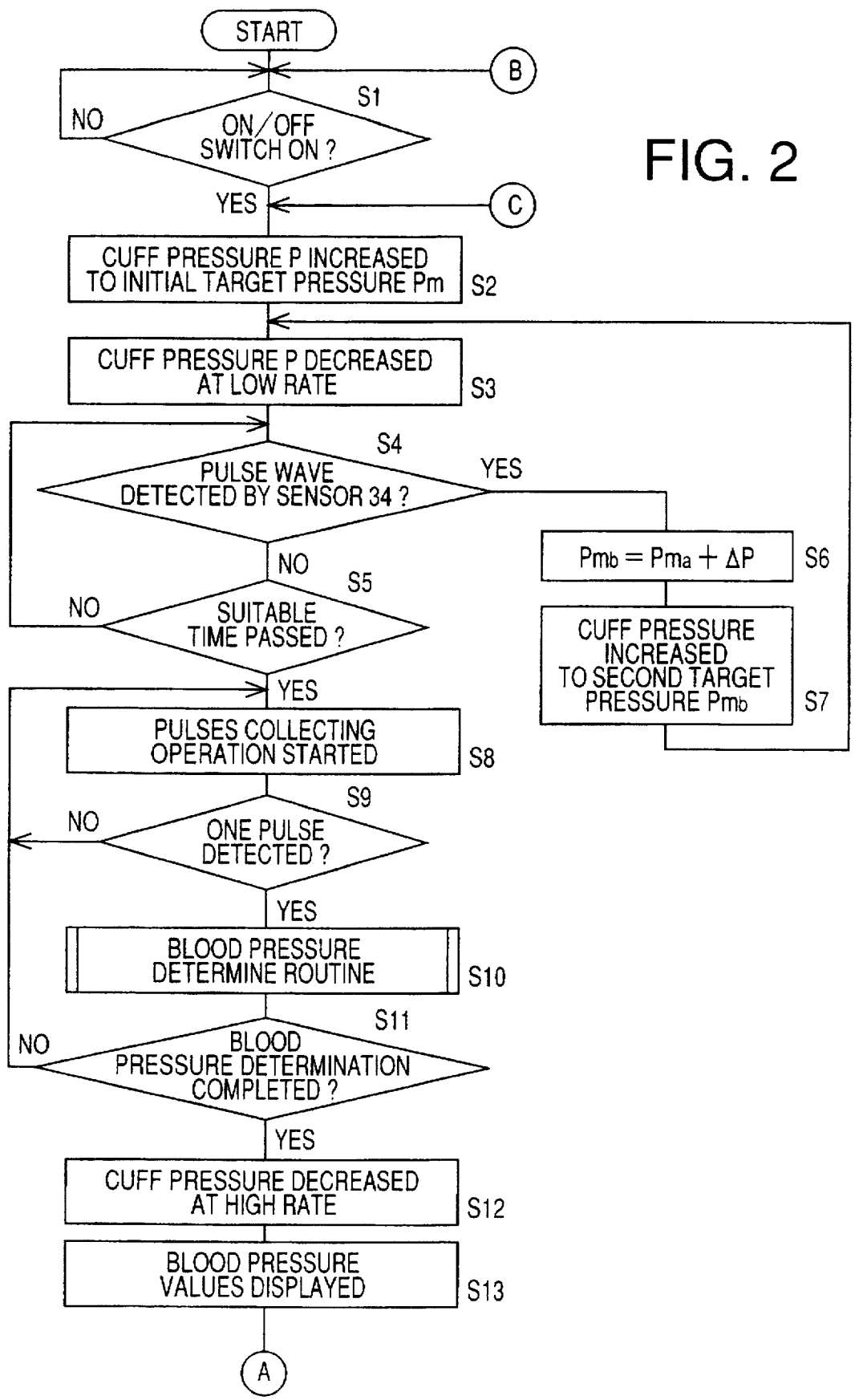
FIG. 2 is a flow chart representing a part of the control programs according to which the system of FIG. 1 is operated.
Figure 3:
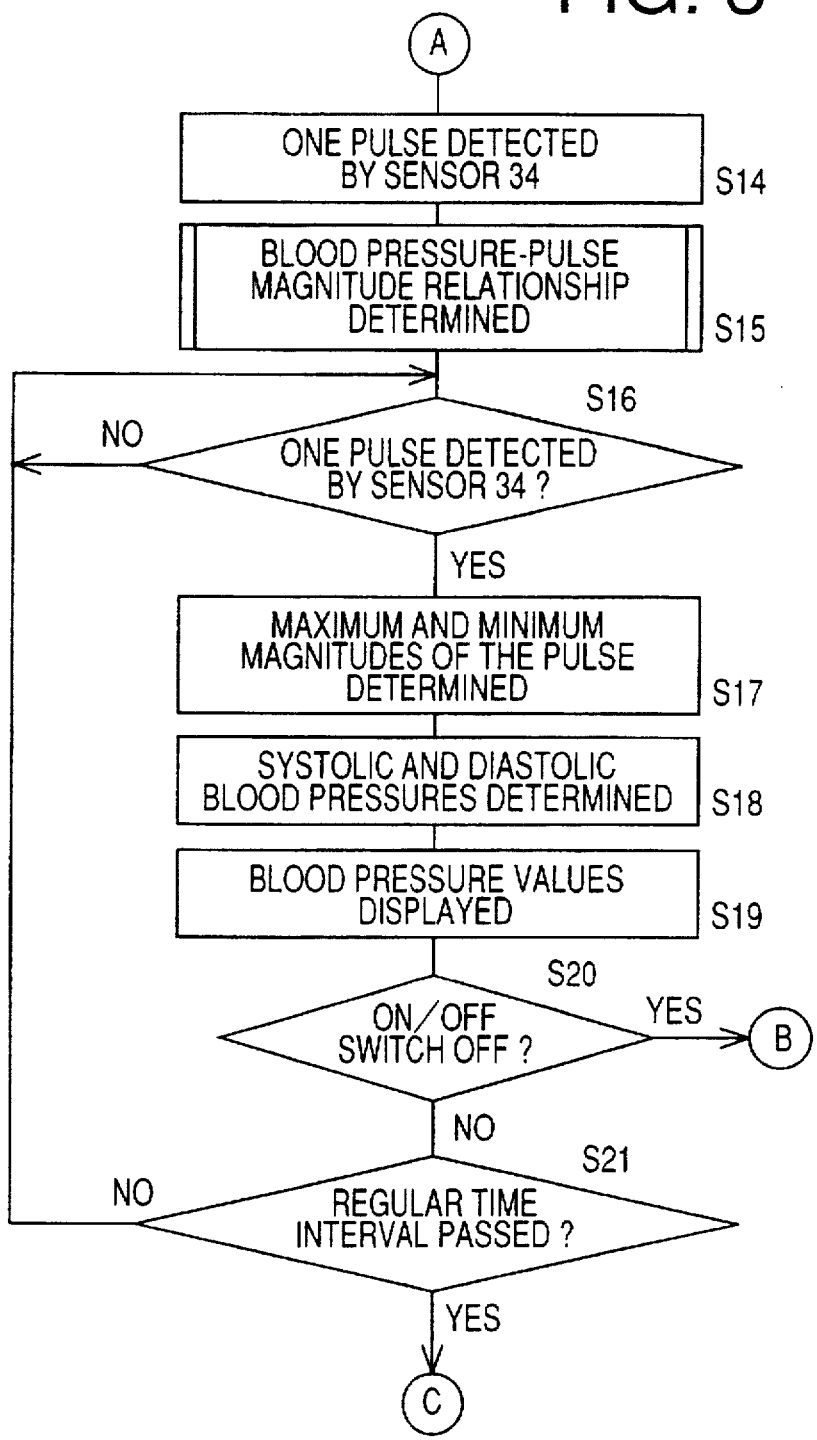
FIG. 3 is a flow chart representing another part of the control programs according to which the system of FIG. 1 is operated.

Next, there will be described the operation of the present monitor system by reference to the flow charts of FIGS. 2 and 3.

Upon application of electric power to the monitor system, the system is initialized, and the control of the CPU of the control device 28 starts with Step S1 to identify whether or not an ON/OFF switch (not shown) has been operated to its ON position. If an negative judgement (NO) is made in Step S1, Step S1 is repeated. On the other hand, if an affirmative judgement (YES) is made in Step S1, the control of the CPU proceeds with Step S2 to place the selector valve 16 in its INFLATION position and activate the air pump 18 so as to increase the cuff pressure P to a predetermined, initial target pressure, Pm, (e.g., 180 mmHg) and subsequently to deactivate the air pump 18. Step S2 is followed by Step S3 to place the selector valve 16 from the INFLATION position to the SLOW-DEFLATION position so as to start decreasing the cuff pressure P at a predetermined, low rate.

Step S3 is followed by Step S4 to identify whether or not the pulse wave sensor 34 has detected the distal pulse wave. If the initial target pressure Pm is higher than a systolic blood pressure of the subject and therefore the blood flow through the brachial artery is completely stopped under the pressure produced by the cuff 10, a negative judgement is made in Step S4. In this case, the control goes to Step S5 to identify whether or not an appropriate time has passed from the starting of the cuff pressure decreasing operation. This appropriate time may be a predetermined time duration measured from the starting of the cuff pressure decreasing operation, a time duration necessary for a predetermined number of pulses to occur, or a time duration necessary for the cuff pressure P to be decreased by a predetermined amount. If the appropriate time has not passed and therefore a negative judgement is made in Step S5, Steps S4 and S5 are repeated. On the other hand, if the time has passed and an affirmative judgement is produced in Step S5, the control goes to Step S8 to start reading in pulses of the pulse wave produced from the brachial artery and transmitted to the cuff 10. That is, the control device 28 does not read in pulses of the pulse wave during the above-indicated appropriate time after the starting of the cuff pressure decreasing operation. The pulses (that is, electric signal $SM_1$) read in in Step S8 are stored for being used for the blood pressure determination in Step S10.

On the other hand, if the pulse wave sensor 34 has detected the distal pulse wave during the above-indicated appropriate time and therefore an affirmative judgement is made in Step S4, that means that a target pressure, $Pm_a$, (target pressure Pm for the initial control cycle) from which the cuff pressure decreasing operation started, that is, a cuff pressure from which the pulses collecting operation is started in Step S8, is lower than a systolic blood pressure of the subject, that is, insufficiently low. Consequently, the control goes to Steps S6 and S7. In Step S6, a predetermined pressure amount, $\Delta P$, (e.g., 10 mmHg) is added to the first target pressure $Pm_a$ for the present control loop so as to provide a second target pressure $Pm_b$, which is to be used as the first target pressure $Pm_a$ if another affirmative judgement is made with respect thereto in Step S4 in the following control loop. Step S6 is followed by Step S7 to place the selector valve 16 from the SLOW-DEFLATION position to the INFLATION position and activate the air pump 18. Subsequently, the control goes back to Step S3 and the following steps. In this control loop, if another affirmative judgement is made in Step S4, the control goes to Steps S6 and S7 to increase the cuff pressure P to a new second target pressure $Pm_b$, higher by the predetermined amount $\Delta P$ than the first target pressure $Pm_a$, that is, the cuff pressure at the time of starting of the cuff pressure decreasing operation in Step S3 at the present control loop, that is, the second target pressure $Pm_b$ determined in Step S7 at the preceding control loop. Subsequently, in Step S3 at the following control loop, the cuff pressure P is decreased from a new first target pressure $Pm_a$, that is, the above-indicated new second target pressure $Pm_b$. Thus, the present monitor system identifies whether or not the first target pressure $Pm_a$ where the cuff pressure decreasing operation is started is insufficiently low, after the cuff pressure decreasing operation has been started and before the blood pressure determination or, more specifically, the pulses collecting operation is started. If the first target pressure $Pm_a$ is found to be insufficiently low, the monitor system continues to increase the cuff pressure P up to a pressure level sufficiently higher than the systolic blood pressure.

After in Step S8 the control device 28 starts reading in pulses of the pulse wave transmitted to the cuff 10, the control goes to Step S9 to identify whether or not the control device 28 has read in one pulse (that is, signal $SM_1$ representing one pulse) of the pulse wave transmitted to the cuff 10. If a negative judgement is made in Step S9, Steps S8 and S9 are repeated. On the other hand, if the control device 28 has read in one pulse of the pulse wave and therefore an affirmative judgement is made in Step S9, the control goes to Step S10 to effect the blood pressure determine routine. This routine is a well-known oscillometric blood pressure measure algorithm in which mean, systolic and diastolic blood pressures are determined by utilizing variation of respective amplitudes of the detected pulses with respect to variation in the cuff pressure P. More specifically described, the control device 28 finds a pulse having the greatest amplitude of the amplitudes of the pulses detected during the cuff pressure decreasing operation (hereinafter, abbreviated to the "maximum pulse"), and determines as a mean blood pressure of the subject a cuff pressure at the time of detection of the maximum pulse. In addition, the control device 28 determines as a systolic blood pressure of the subject a cuff pressure at the time of an inflection point of a curve representing the variation of the pulse amplitudes which point is positioned on a higher-pressure side of the mean blood pressure, and as a diastolic blood pressure of the subject a cuff pressure at the time of an inflection point of the curve positioned on a lower-pressure side of the mean blood pressure. Subsequently, the control goes to Step S11 to identify whether or not the blood pressure determination has been completed. If a negative judgement is made in Step S11, Steps S8 through S11 are repeated. On the other hand, if the blood pressure determination has been completed and therefore an affirmative judgement is made in Step S11, the control of the CPU goes to Step S12 to switch the selector valve 16 from the SLOW-DEFLATION position to the RAPID-DEFLATION position so as to decrease the cuff pressure P at a high rate. Subsequently, the control proceeds to Step S13 to indicate the determined blood pressure values on the display 32.

Next, the control of the CPU goes to Step S14 to read in one pulse of the distal pulse wave detected by the pulse wave sensor 34, that is, electric signal $SM_2$ representing the pulse. Subsequently, the control goes to Step S15 to determine a relationship between blood pressure and magnitude of pulse (that is, magnitude of signal $SM_2$). More specifically described, the control device 28 determines a maximum and a minimum magnitude (that is, upper and lower peak magnitudes) of the pulse detected in Step S14, and determines a linear function by using the determined maximum and minimum pulse magnitudes and the systolic and diastolic blood pressures determined in Step S10. This method is described in detail in U.S. Pat. No. 5,139,026, the assignee of which is the assignee of the present application.

Step S15 is followed by Step S16 to identify whether or not the pulse wave sensor 34 has detected one pulse of the distal pulse wave. If a negative judgement is made in Step S16, Step 16 is repeated. Meanwhile, if the pulse wave sensor 34 has detected a pulse and accordingly an affirmative judgement is made in Step S16, the control goes to Step S17 to determine a maximum and a minimum magnitude of the detected pulse and subsequently to Step S18 to determine a systolic and a diastolic blood pressure of the subject by using the blood pressure-pulse magnitude relationship determined in Step S15 and the maximum and minimum pulse magnitudes determined in Step S17. Further, in Step S19, the control device 28 commands the display 32 to indicate the determined blood pressure values.

Subsequently, the control goes to Step S20 to identify whether or not the ON/OFF switch has been operated to its OFF position. If a negative judgement is made in Step S20, the control goes to Step S21 to identify whether or not a predetermined regular interval (e.g., 5 to 10 minutes) has passed. If a negative judgement is made in Step S21, the control goes back to Step S16 and the following steps to determine a systolic and a diastolic blood pressure of the subject by using the relationship determined in Step S15 and a maximum and a minimum magnitude of each of pulses detected by the pulse wave sensor 34 after determination of the relationship, and continuously indicate on the display 32 the blood pressure values determined with respect to the each pulse. On the other hand, if an affirmative judgement is made in Step S21, the control goes back to Step S2 and the following steps to measure a systolic and a diastolic blood pressure of the subject using the cuff 10 in Step 10, update the blood pressure-pulse magnitude relationship in Step S15, and monitor the blood pressure of the subject using the pulse wave sensor 34 in Step S18. Meanwhile, if the ON/OFF switch is operated to the OFF position and an affirmative judgement is made in Step S20, the control goes to Step S1 to wait for operation of the ON/OFF switch to the ON position.

As is apparent from the foregoing description, in the present blood pressure monitor system, the pulse wave sensor 34 is set over the radial artery which is continuous with the brachial artery pressed by the cuff 10 and is located on the distal side of the cuff 10 as seen from the heart of the subject, so that the sensor 34 detects the distal pulse wave from the radial artery. If the pulse wave sensor 34 detects the distal pulse wave after the cuff pressure P has been increased to the first target pressure $Pm_a$ and before the control device 28 starts collecting pulses of the pulse wave transmitted to the cuff 10, the monitor system identifies that the first target pressure $Pm_a$ is insufficiently low. In this case, the monitor system increases the cuff pressure P to the second target pressure $Pm_b$ higher by the predetermined pressure amount than the first target pressure $Pm_a$ and, by repeating this operation as needed, the monitor system increases the cuff pressure P up to a pressure level sufficiently higher than the systolic pressure of the subject. Thus, the present system completes the blood pressure determination in a reduced time as compared with a conventional apparatus of the type which does not identify whether or not a target pressure is insufficiently low until cuff pressure is decreased to a pressure level equal to a mean blood pressure of the subject.

Since, in the present embodiment, whether the first target pressure $Pm_a$ is insufficient or not is identified after the starting of the cuff pressure decreasing operation and before the starting of the pulses collecting operation, the blood pressure determination is completed in a still shorter time than in a manner where the identification is made before the starting of the cuff pressure decreasing operation. However, it is possible to adapt the present embodiment to make this identification before the starting of the cuff pressure decreasing operation.

In addition, in the present embodiment, the pulse wave sensor 34 provided for monitoring the blood pressure of a subject serves also as the distal pulse wave detecting means used for identifying whether the first target pressure $Pm_a$ is insufficient or not. This arrangement contributes to simplifying the construction of the monitor system.

While, in the illustrated embodiment, the pulse wave sensor 34 is pressed on the wrist 40 with a pressing force produced by the band 38, it is possible to use, in place of the band 40, an exclusive pressing device disclosed in the above-indicated U.S. Pat. No. 5,139,026. This pressing device includes a housing adapted to be set on, for example, a wrist with the help of a band, and the pulse wave sensor is supported by the housing so as to be advanceable from an open end of the housing. In this case, the pressing force applied to the pulse wave sensor is adjusted by changing air pressure in a chamber defined in the housing.

Although, in the illustrated embodiment, the pulse wave sensor 34 detects the distal pulse wave from the radial artery, it is possible to use means for detecting a pulse wave from a digital artery located at a more distal position than the radial artery. Alternatively, it is possible to press using a cuff a femoral artery and detect using a pulse wave sensor a pulse wave from a dorsal artery of foot located on a distal side of the femoral artery pressed by the cuff.

Furthermore, in place of the pulse wave sensor 34 detecting a pressure pulse wave, it is possible to employ, as the distal pulse wave detecting means, an oximeter which optically detects a blood oxygen saturation of the subject. The blood oxygen saturation detected by the oximeter can be used as distal pulse wave for identifying whether or not the first target pressure $Pm_a$ is insufficiently low.

Although, in the illustrated embodiment, Steps S8 and S9 are effected after Steps S3 through S7, it is possible to carry out Steps S8 and S9 concurrently with Steps S3 through S7.

The illustrated monitor system iteratively effects blood pressure determinations at predetermined regular intervals of time by using the cuff 10, and monitor the blood pressure of a subject by determining systolic and diastolic blood pressures with respect to each of pulses of a pulse wave detected by the pulse wave sensor 34. However, the principle of the present invention is applicable to other types of blood pressure measuring apparatus, for example, an apparatus of the type which uses a pulse wave sensor exclusively for identifying whether or not the first target pressure $Pm_a$ is insufficient or not. In this case, the apparatus may be of the type which carries out the blood pressure determination only one time in response to one-time operation of the ON/OFF switch.

It is to be understood that the present invention may be embodied with various changes, improvements and modifications that may occur to those skilled in the art without departing from the scope and spirit of the invention defined in the appended claims.

What is claimed is:

1. An automatic blood pressure measuring system for measuring a blood pressure of a living subject by an oscillometric method in which a blood pressure is determined by utilizing a pulse wave comprising pulses produced from an arterial vessel of the subject in synchronism with a heartbeat of the subject, the apparatus comprising:

an inflatable cuff adapted to be wound around an upper arm of a subject, for pressing said upper arm and thereby pressing a brachial artery extending in said upper arm of said subject;

regulating means for regulating a pressing force of said cuff;

oscillometric blood-pressure measuring means comprising control means for controlling said regulating means to increase said pressing force of said cuff to a first target force, a first pulse wave sensor associated with said cuff, for collecting pulses of a first pressure pulse wave which are produced from said brachial artery and transmitted to said cuff when said pressing force is decreased from said first target force, and means for determining a blood pressure of said subject by an oscillometric method using the collected pulses;

a second pulse wave sensor for detecting a second pressure pulse wave from a radial artery which is continuous with said brachial artery of said subject and is located on a distal side of said brachial artery as seen from the heart of said subject, said second pulse wave sensor being adapted to be pressed against said radial artery via skin tissue of said subject for detecting the second pressure pulse wave therefrom, said second pulse wave sensor being apart from said cuff;

first determining means for determining a magnitude of the second pressure pulse wave which is detected from said radial artery by said second pulse wave sensor when said brachial artery is not pressed by said cuff;

second determining means for determining a relationship between blood pressure and pulse magnitude by using the blood pressure measured by said measuring means and the determined magnitude of said second pressure pulse wave;

third determining means for determining a magnitude of each of pulses of said second pressure pulse wave which are detected from said radial artery by said second pulse wave sensor after the determination of said relationship and when said brachial artery is not pressed by said cuff;

fourth determining means for determining a blood pressure of said subject by using the determined relationship and the determined magnitude of said each pulse; and increasing means for increasing said pressing force to a second target force greater by a predetermined amount than said first target force, in response to detection of presence of the second pressure pulse wave by said second pulse wave sensor from said radial artery after said regulating means has increased said pressing force of said cuff to said first target force for pressing said brachial artery and before said measuring means determines said blood pressure of said subject, wherein said first pulse wave sensor of said measuring means starts collecting the pulses transmitted to said cuff, if said second pulse wave sensor does not detect the second pressure pulse wave from said radial artery before a predetermined time has passed after said pressing force of said cuff begins to decrease from said first target force.

2. The system as set forth in claim 1, wherein said increasing means continues to increase said pressing force by increments of said predetermined amount until said second pulse wave sensor does not detect the second pressure pulse wave from said radial artery.

3. The system as set forth in claim 1, further comprising means for supplying said cuff with pressurized fluid for inflating the cuff and thereby pressing said upper arm and said brachial artery.

4. The system as set forth in claim 1, wherein said measuring means determines a systolic and a diastolic blood pressure of said subject, said first determining means determines a maximum and a minimum magnitude of a pulse of said second pressure pulse wave detected by said pulse wave sensor, said second determining means determines the blood pressure-pulse magnitude relationship by using the systolic and diastolic blood pressures determined by said measuring means and the determined maximum and minimum pulse magnitudes, said third determining means determines a maximum and a minimum magnitude of said each second pulse of said second pressure pulse wave detected by said pulse wave sensor after the determination of said blood pressure-pulse magnitude relationship, and said fourth determining means determines a systolic and a diastolic blood pressure of said subject by using said blood pressure-pulse magnitude relationship and said maximum and minimum magnitude of said each pulse of said second pressure pulse wave.

5. The system as set forth in claim 1, wherein said measuring means determines said blood pressure of said subject at predetermined regular intervals of time, said second determining means updates said blood pressure-pulse magnitude relationship by using each of the blood pressures determined at said regular intervals and a determined magnitude of said second pressure pulse wave, said third determining means determines a magnitude of each of pulses of said second pressure pulse wave detected after each updating of said relationship, and said fourth determining means determines a blood pressure of said subject by using said each updated relationship and the determined magnitude of said each pulse.

6. The system as set forth in claim 1, wherein said second determining means determines said blood pressure-pulse magnitude relationship such that blood pressure is a linear function of pulse magnitude.

7. The system as set forth in claim 1, further comprising display means for displaying said blood pressure determined by said measuring means and said blood pressure determined by said fourth determining means.

8. An automatic blood pressure measuring system for measuring a blood pressure of a living subject by an oscillometric method in which a blood pressure is determined by utilizing a pulse wave comprising pulses produced from an arterial vessel of the subject in synchronism with a heartbeat of the subject, the apparatus comprising:

an inflatable cuff adapted to be wound around an upper arm of a subject, for pressing said upper arm and thereby pressing a brachial artery extending in said upper arm of said subject;

regulating means for regulating a pressing force of said cuff;

oscillometric blood-pressure measuring means comprising control means for controlling said regulating means to increase said pressing force of said cuff to a first target force, a first pulse wave sensor associated with said cuff, for collecting pulses of a first pressure pulse wave which are produced from said brachial artery and transmitted to said cuff when said pressing force is decreased from said first target force, and means for determining a blood pressure of said subject by an oscillometric method using the collected pulses;

a second pulse wave sensor for detecting a second pressure pulse wave from a radial artery which is continuous with said brachial artery of said subject and is located on a distal side of said brachial artery as seen from the heart of said subject, said second pulse wave sensor being adapted to be pressed against said radial artery via skin tissue of said subject for detecting the second pressure pulse wave therefrom, said second pulse wave sensor being apart from said cuff;

first determining means for determining a magnitude of the second pressure pulse wave which is detected from said radial artery by said second pulse wave sensor when said brachial artery is not pressed by said cuff;

second determining means for determining a relationship between blood pressure and pulse magnitude by using the blood pressure measured by said measuring means and the determined magnitude of said second pressure pulse wave;

third determining means for determining a magnitude of each of pulses of said second pressure pulse wave which are detected from said radial artery by said second pulse wave sensor after the determination of said relationship and when said brachial artery is not pressed by said cuff;

fourth determining means for determining a blood pressure of said subject by using the determined relationship and the determined magnitude of said each pulse; and increasing means for increasing said pressing force to a second target force greater by a predetermined amount than said first target force, in response to detection of presence of the second pulse wave by said second pulse wave sensor from said radial artery after said regulating means has increased said pressing force of said cuff to said first target force for pressing said brachial artery and before said measuring means determines said blood pressure of said subject, wherein any second pulse wave detected by the second pulse wave sensor before passing of a predetermined time is excluded from the blood pressure determination.

9. The system as set forth in claim 8, wherein said increasing means continues to increase said pressing force by increments of said predetermined amount until said second pulse wave sensor does not detect the second pressure pulse wave from said radial artery.

10. The system as set forth in claim 8, further comprising means for supplying said cuff with pressurized fluid for inflating the cuff and thereby pressing said upper arm and said brachial artery.

11. The system as set forth in claim 8, wherein said measuring means determines a systolic and a diastolic blood pressure of said subject, said first determining means determines a maximum and a minimum magnitude of a pulse of said second pressure pulse wave detected by said second pulse wave sensor, said second determining means determines the blood pressure-pulse magnitude relationship by using the systolic and diastolic blood pressures determined by said measuring means and the determined maximum and minimum pulse magnitudes, said third determining means determines a maximum and a minimum magnitude of said each pulse of said second pressure pulse wave detected by said second pulse wave sensor after the determination of said blood pressure-pulse magnitude relationship, and said fourth determining means determines a systolic and a diastolic blood pressure of said subject by using said blood pressure-pulse magnitude relationship and said maximum and minimum magnitudes of said each pulse of said second pressure pulse wave.

12. The system as set forth in claim 8, wherein said measuring means determines said blood pressure of said subject at predetermined regular intervals of time, said second determining means updates said blood pressure-pulse magnitude relationship by using each of the blood pressures determined at said regular intervals and a determined magnitude of said second pressure pulse wave, said third determining means determines a magnitude of each of pulses of said second pressure pulse wave detected after each updating of said relationship, and said fourth determining means determines a blood pressure of said subject by using said each updated relationship and the determined magnitude of said each pulse.

13. The system as set forth in claim 8, wherein said second determining means determines said blood pressure-pulse magnitude relationship such that blood pressure is a linear function of pulse magnitude.

14. The system as set forth in claim 8, further comprising display means for displaying said blood pressure determined by said measuring means and said blood pressure determined by said fourth determining means.

* * * * *